US011345959B2

(12) United States Patent
Lee et al.

(10) Patent No.: US 11,345,959 B2
(45) Date of Patent: May 31, 2022

(54) METHOD FOR EXPLORING USEFUL GENETIC RESOURCES THROUGH BULK METAGENOME ANALYSIS AND USE THEREOF

(71) Applicant: Dong Woo Lee, Daegu (KR)

(72) Inventors: Dong Woo Lee, Daegu (KR); Yong Jik Lee, Daegu (KR); Sang Jae Lee, Busan (KR); Han Seung Lee, Busan (KR)

(73) Assignee: Done Woo Lee, Daegu (KR)

( * ) Notice: Subject to any disclaimer, the term of this patent is extended or adjusted under 35 U.S.C. 154(b) by 216 days.

(21) Appl. No.: 15/756,441

(22) PCT Filed: Jun. 24, 2016

(86) PCT No.: PCT/KR2016/006792
§ 371 (c)(1),
(2) Date: Feb. 28, 2018

(87) PCT Pub. No.: WO2016/209037
PCT Pub. Date: Dec. 29, 2016

(65) Prior Publication Data
US 2018/0230528 A1 Aug. 16, 2018

(30) Foreign Application Priority Data

Jun. 24, 2015 (KR) .................. 10-2015-0089772
Jun. 24, 2016 (KR) .................. 10-2016-0079254

(51) Int. Cl.
C12Q 1/6869 (2018.01)
C12Q 1/6806 (2018.01)
C12Q 1/6844 (2018.01)
C12Q 1/6888 (2018.01)

(52) U.S. Cl.
CPC ......... C12Q 1/6869 (2013.01); C12Q 1/6806 (2013.01); C12Q 1/6844 (2013.01); C12Q 1/6888 (2013.01)

(58) Field of Classification Search
CPC .. C12Q 1/6869; C12Q 1/6806; C12Q 1/6844; C12Q 1/686
See application file for complete search history.

(56) References Cited

U.S. PATENT DOCUMENTS 7,872,100 B2 * 1/2011 Verseck ......... C12Y 402/01084
530/350
9,783,859 B2 10/2017 Lee et al.

FOREIGN PATENT DOCUMENTS

KR 1020090097056 9/2009
KR 1020110073049 6/2011

OTHER PUBLICATIONS

Yamazaki et al. Planta 2001; 214: 75-84 (Year: 2001).*
Bracchi et al. Molecular and Biochemical Parasitology 1996; 76: 299-303 (Year: 1996).*
Deng et al. The Journal of Biological Chemistry 2010; 285: 30181-30191 (Year: 2010).*
Fernandes et al. Antonie van Leeuwenhoek 2014; 106: 391-398 (Year: 2014).*
Gen Bank Accession No. KJ149474.1 for Streptomyces araujoniae multicopper oxidase superfamily Kgene, partial cds, Aug. 7, 2014 [online], [retrieved on Mar. 2, 2020], retrieved from the Internet: <URL: www.ncbi.nlm.nih.gov/nuccore/KJ149474.1 ?report=genbank> (Year: 2014).*
Gen Bank Accession No. KJ149471.1 for *Streptomyces* sp. SB035 multicopper oxidase superfamily Kgene, partial cds, Aug. 7, 2014 [online], [retrieved on Mar. 2, 2020], retrieved from the Internet: <URL: www.ncbi.nlm.nih.gov/nuccore/KJ149471.1 ?report=genbank> (Year: 2014).*
Wilson, M.C. & Piel, J. Metagenomic Approaches for Exploiting Uncultivated Bacteria as a Resource for Novel Biosynthetic Enzymology. Chemistry & Biology 2013; 20: 636-647 (Year: 2013).*
Rose et al. Consensus-degenerate hybrid oligonucleotide primers for amplification of distantly related sequences. Nucleic Acids Research 1998; 26: 1628-1635 (Year: 1998).*
Wilkie et al. Design of degenerate oligonucleotide primers for cloning of G-protein alpha subunits. Methods in Enzymology 1994; 237: 327-344 (Year: 1994).*
Abd-Elsalam, K.A. Bioinformatic tools and guideline for PCR primer design. African Journal of Biotechnology 2003; 2: 91-95 (Year: 2003).*
Niehaus et al. Enzymes for the laundry industries: tapping the vast metagenomic pool of alkaline proteases. Microbial Biotechnology 2011; 4: 767-776 (Year: 2011).*
Kotik et al. Sequence diversity in haloalkane dehalogenases, as revealed by PCR using family-specific primers. Journal of Microbiological Methods 2012; 88: 212-217 (Year: 2012).*
Bergkemper et al. Novel oligonucleotide primers reveal a high diversity of microbes which drive phosphorous turnover in soil. Journal of Microbiological Methods 2016; 125: 91-97 (Year: 2016).*
Foissac et al. Polyvalent Degenerate Oligonucleotides Reverse Transcription-Polymerase Chain Reaction: A Polyvalent Detection and Characterization Tool for Trichoviruses, Capilloviruses, and Foveaviruses Phytopathology 2005; 95: 617-625 (Year: 2005).*

(Continued)

Primary Examiner — Angela M. Bertagna
(74) Attorney, Agent, or Firm — Sughrue Mion, PLLC

(57) ABSTRACT

Provided is a method for analyzing metagenomic information using a degenerate primer which can be applied for quickly determining the utility value of a massive amount of metagenome samples. In particular, the superfamily-specific degenerate primer of the present invention is used to quickly detect the presence or absence of the genetic information of the target peptides in the metagenome by a simple method, thereby collecting a large amount of useful peptide resource information from various metagenome samples at high speed. Further, the present invention may be used for screening new peptide genes by designing and producing superfamily-specific degenerate primers of new target peptides based on the method of the present invention. In addition, the method of the present invention can be applied not only to enzymes but also to studies related to polypeptides, oligopeptides, antibiotic resistance genes, antimicrobial peptides, antifungal peptides, oligopeptides, markers, or single-nucleotide polymorphism (SNP).

4 Claims, 6 Drawing Sheets
Specification includes a Sequence Listing.

(56) References Cited

OTHER PUBLICATIONS

Iserte et al., "Family-Specific Degenerate Primer Design: A Tool to Design Consensus Degenerated Oligonucleotides," Biotechnology Research International, 9 pages (2013).
Roh et al., "Screening and purification for novel cytochrome $b_5$ from uncultured environmental micro-organisms," Letters in Applied Microbiology 44:475-480 (2007).

* cited by examiner

[FIG. 1]

[FIG. 3]
A
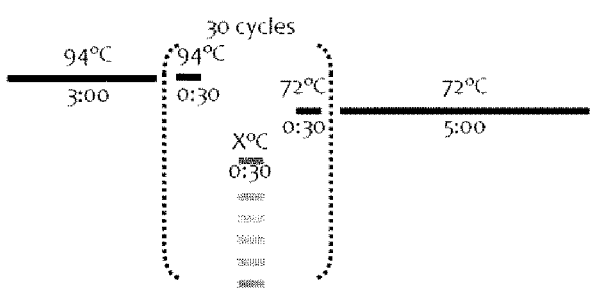
58°C: gabT, wegB, araA
56°C: aprE, pyrK, galE
54°C: katE, catA
52°C: phy, ytoP
51°C: tpiA, polA
47°C: eglS
B
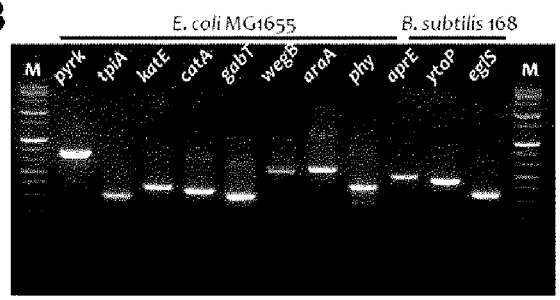
| Genes | No. of samples | Target genes confirmed |
|---|---|---|
| pyrk | 6 | 6 |
| tpiA | 3 | 3 |
| katE | 11 | 8(2) |
| catA | 3 | 3 |
| gabT | 2 | 2 |
| wegB | 2 | 2 |
| araA | 2 | 2 |
| phy | 2 | 2 |
| aprE | 2 | 2 |
| ytoP | 4 | 3 |
| eglS | 3 | 3 |
|  | 40 | 37 (92.5%) |
C  Annealing Tm. : 70 °C
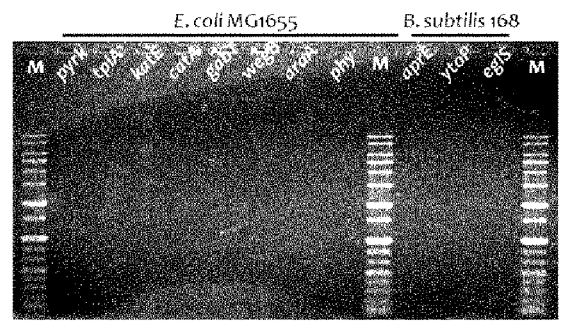

[FIG. 4]
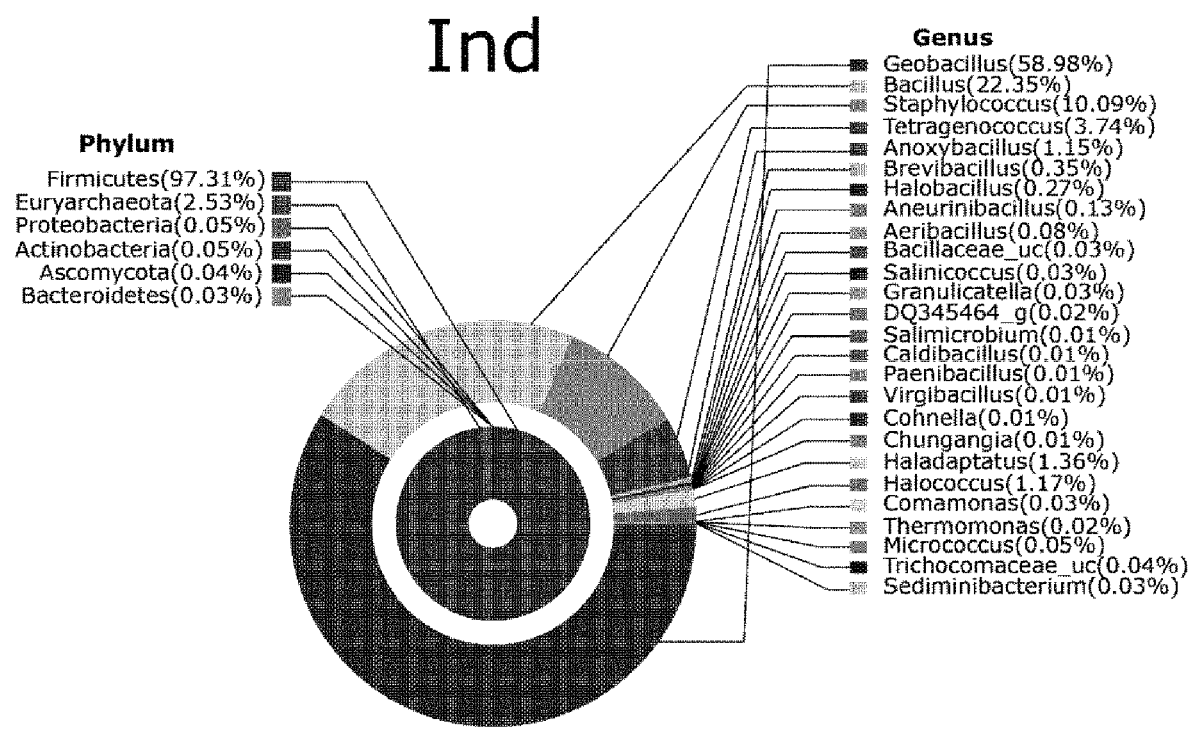

[FIG. 5]
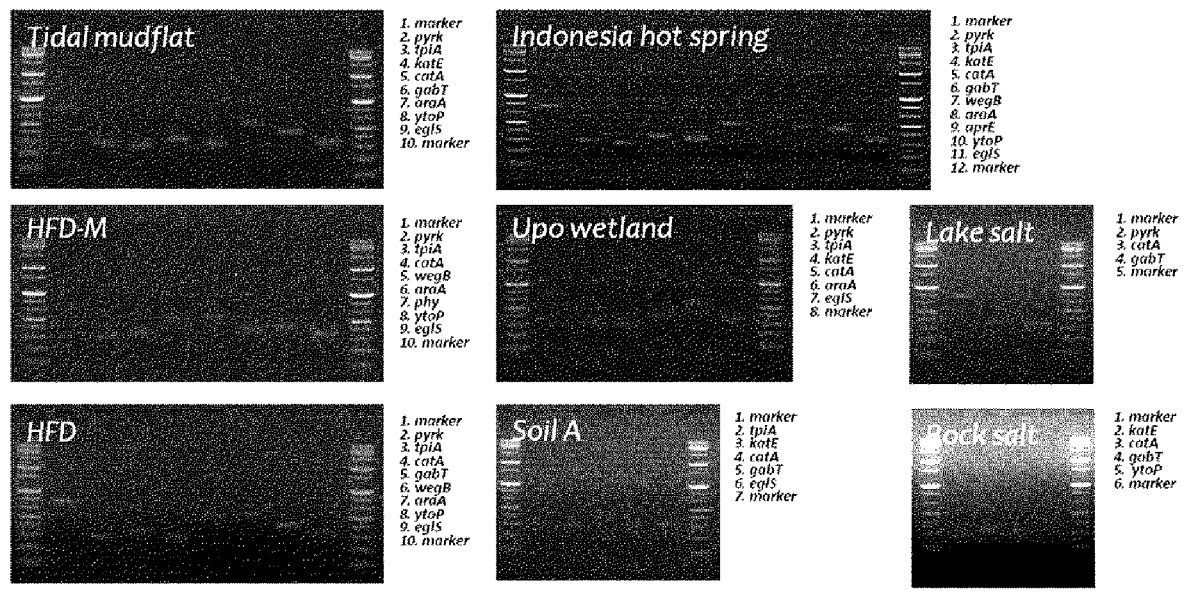

[FIG. 6]
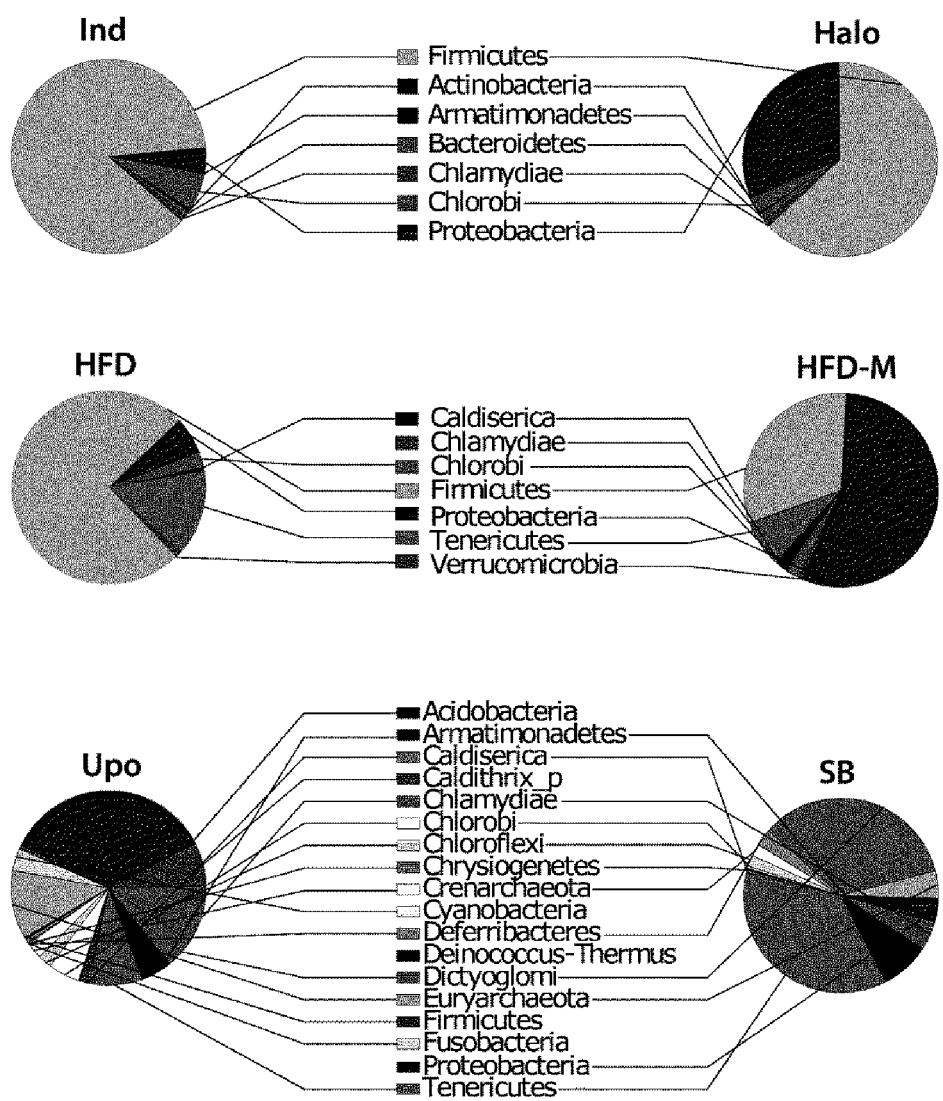

METHOD FOR EXPLORING USEFUL GENETIC RESOURCES THROUGH BULK METAGENOME ANALYSIS AND USE THEREOF

TECHNICAL FIELD

The present invention relates to a method for high-throughput screening useful gene products by metagenomics analysis and a use thereof.

BACKGROUND ART

A metagenome is defined as a set of genomes of all microorganisms present in a specific natural environment. Although microorganisms are the largest portion of all organisms, it is difficult to provide conditions similar to the original natural environment in which microorganisms are present. Thus, more than 99% of the microorganisms present in the environment cannot be cultured in a laboratory. When using the metagenome, DNA can be directly extracted from various microorganisms existing in natural environment regardless of whether it can be cultured in a laboratory, thereby enabling gene screening, identification, and function analysis.

Through the analysis of such metagenome samples, the role of the microorganisms in specific environments can be revealed so that microorganisms are used to help all fields related to human life such as industry, environment, energy, agriculture, and medical care, for example, wastewater treatment, chemical compound production, pharmaceutical production, bioenergy production, and industrial process. Recent metagenomic studies are attractive because they are useful for the search of novel materials or new enzymes as an applicable field as mentioned above. In particular, enzymes are biocatalysts prepared by living organisms, and enzymes derived from microorganisms and metagenomes have been attempted to use in catalytic reactions required in chemical synthesis processes. Enzymes are very useful in various industrial fields because they have very high precision, specificity, selectivity, and high efficiency compared to chemical catalysts. The catalytic efficiency of enzymes is $10^8$ to $10^{14}$ times higher than that of the non-enzymatic reaction under similar reaction conditions, and the selectivity of the reaction thereof is very high compared to that of the chemical catalytic reaction. In addition, if an enzyme capable of reacting exists under even special conditions such as reaction under high temperature, high pressure, and organic solvent, it is an item having a very high utility value as a product for the future industry.

Because the economic feasibility of the enzyme was so low in the beginning, it was difficult to use it. However, the remarkable development of novel technologies including gene manipulation technology, biotechnology, and molecular evolution technology results in high-throughput screening and its improvement for developing new functional enzymes, thereby expanding the application to new application field.

The method of measuring the presence or activity of enzymes for screening such enzymes includes screening methods using a microorganism and utilizing a non-culturable metagenome. In the case of the former, various strains collection is mandatory, and selection of candidate strains should be preceded by direct cultivation and activity comparison of these strains. In addition, there is a drawback that it requires a lot of labor and research expenses and takes a long time. In order to address these issues, a high-throughput screening system has been developed and utilized. However, in order to identify the desired useful enzyme, it is necessary to purify genomic DNA (gDNA) from a candidate strain, to construct a DNA library, to reconfirm the activity of enzymes utilizing expression system, and to reanalyze nucleotide sequence of selected library strain, thereby ensuring the desired useful enzyme resources. In the latter case, the DNA library is constructed using a metagenome purified from gDNA directly from an environmental sample. This method can also be classified as functional-based enzyme screening in which the activity thereof is compared using the expression system or DNA sequence-based enzyme screening in which DNA of the desired useful enzyme resources is secured using degeneracy primers. In the case of an enzyme screening method based on its activity, a library is prepared by direct cloning of the metagenome and then it is directly confirmed that an enzyme which reacts with the substrate through expression to convert it into a desired substance exists. Although this method has the advantage of surely confirming the existence of gene resource, a considerable amount of labor and time is invested in the process of preparing and expressing the library, and *Escherichia coli* system is mainly used for the expression system, thereby having a limitation of the heterologous gene expression system. In the case of a bacterial gene that has a far evolutionary relationship from the same, in which the construction or use of its promoter or codon does not match with *Escherichia coli*, there are disadvantages that the expression of the gene may be affected, and the efficiency of screening is lower compared to its effort and investment. In the case of an enzyme screening method based on a nucleotide sequence, the nucleotide sequence of the target enzyme is confirmed by a polymerase chain reaction using a primer constructed based on the specific motif of the target enzyme. However, since this method also uses a primer based on the motif of a specific enzyme, there are issues that the obtained nucleotide sequence is biased to anyone enzyme to be amplified, and the nucleotide sequence should be confirmed by directly sequencing the DNA library including the target enzyme.

Polymerase chain reaction (PCR) is a gene detection method in which a specific deoxyribonucleic acid region is amplified by a polymerase in vitro. The polymerase chain reaction is an enzymatic reaction for several hours, thereby resulting in the explosive mass production of the gene and has become a critical technique for the highly-applicable deoxyribonucleic acid detection so that it has become an essential technology in all life science fields requiring molecular biology approaches. Meanwhile, the term of "degeneracy" refers to a phenomenon in which one kind of amino acid corresponds to a plurality of codons. The degeneracy does not lead to determine the nucleotide sequence of a gene encoding any particular amino acid sequence but allows to synthesize oligonucleotides including all possible nucleotide sequences. When a polymerase chain reaction is performed using a degenerate oligonucleotide as a primer, a DNA fragment of a gene encoding the protein may be obtained based on amino acid sequence information. Primers designed for such purpose refer to degenerate primers, and its polymerase chain reaction refers to degenerate polymerase chain reaction. This method is a technique for cloning a gene from an amino acid sequence of a substrate but is now widely used for searching gene families based on information of the primary structure (nucleotide sequence) of an abundantly accumulated nucleic acid. Despite a disadvantage in that the actual presence or activity of the enzyme is unknown, and it must be ultimately confirmed through expression, it has an advantage in that the target DNA can be screened from the metagenome departing from the labor-intensive method.

PRIOR ART DOCUMENT

Korean Patent Application No.: 10-2009-0130204

DISCLOSURE

Technical Problem

Thus, the inventors of the present invention have developed a method for quickly and accurately determining the utility value of a metagenome sample in the screening poly-peptides such as industrially useful enzymes. Further, the inventors have extensively amplified genes of polypeptides such as various enzymes and have designed and prepared a degenerate primer which is superfamily-specific to a target peptide, which is capable of being utilized as bar-code sequence for efficient and quick analysis of massive nucleotide sequences of the amplified fragments. Thus, the method was used for the polymerization chain reaction so that DNA fragments extensively amplified from the metagenome sample were analyzed by a next-generation sequencing, thereby confirming the massive nucleotide sequences of the useful peptides to complete the present invention.

Accordingly, one aspect of the present invention relates to a method for analyzing metagenomic information using a superfamily-specific degenerate primer set to a target gene.

Further, another aspect of the present invention relates to a superfamily-specific degenerate primer set to the target gene.

Technical Solution

One aspect of the present invention relates to a method of analyzing metagenomic information including:
(1) amplifying a gene in a metagenome sample, which is a template, with a superfamily-specific degenerate primer set to a target gene; and
(2) analyzing sequence of the amplificatied product of the gene.

The superfamily-specific degenerate primer set to the target gene may be such that
i) the primer set is specific for a gene encoding a target protein exhibiting amino acid identity of 35% or more;
ii) sequence of the binding site between the primer and the target gene has identity of 80% or more;
iii) a degeneracy ratio is 1,500 or less;
iv) a temperature of annealing is 70° C. or less;
v) a length of the primer is 30 bases or less;
vi) identity of an inside of the primer binding site is 40% or less; and
vii) a size of the amplified fragment is 1,000 bp or less.
More preferably, the degeneracy ratio may be 800 or less; the length of the primer may be 25 bases or less; and the size of the amplified fragment may be 500 bp or less.

The metagenome sample may be a metagenomic library, a vector which the metagenomic library is introduced, or a cell transformed with the vector.

Further, the metagenome sample may be a soil, a wetland, a volcano, a tidal mudflat, a salt pan, fresh water, seawater, a body fluid, urine, an agricultural product, an aquatic product, or feces.

Further, the target gene encodes a polypeptide, an oligopeptide, an enzyme, an antibiotic resistance gene, an antimicrobial peptide, an antifungal peptide, an oligopeptide, or a marker.

Further, the step (2) of analyzing the sequence may use one or more processes selected from the group consisting of single-molecule real-time sequencing, ion semiconductor sequencing, pyrosequencing, sequencing by synthesis (SBS), sequencing by ligation (SBL), and chain termination.

Further, another aspect of the present invention provides a superfamily-specific degenerate primer set to a target gene for analyzing metagenomic information, in which
i) the primer set is specific for a gene encoding a target protein exhibiting amino acid identity of 35% or more;
ii) sequence of the binding site between the primer and the target gene has identity of 80% or more
iii) a degeneracy ratio is 1,500 or less;
iv) a temperature of annealing is 70° C. or less;
v) a length of the primer is 30 bases or less;
vi) identity of an inside of the primer binding site is 40% or less; and
vii) a size of the amplified fragment is 1,000 bp or less.
The degeneracy ratio may be 800 or less;
the length of the primer is 25 bases or less; and
the size of the amplified fragment is 500 bp or less.

Advantageous Effects

The method for the metagenomic information analysis and the primer set used for the method according to the present invention can be applied for quickly determining the utility value of a massive amount of metagenome samples. In particular, the superfamily-specific degenerate primers of the present invention are used to quickly detect the presence or absence of the genetic information of the target peptides in the metagenome by a simple method, thereby collecting a large amount of useful peptide resource information from various metagenome samples at high speed. Further, the present invention may be used for screening new peptide coding genes by designing and producing superfamily-specific degenerate primers of new target peptides based on the method of the present invention. In addition, the method of the present invention can be applied not only to enzymes but also to studies related to polypeptides, oligopeptides, antibiotic resistance genes, antimicrobial peptides, antifungal peptides, oligopeptides, markers or single-nucleotide polymorphism (SNP).

DESCRIPTION OF DRAWINGS

FIG. 3 illustrates the optimum conditions of PCR (A of FIG. 3) thereon, the result thereof (B of FIG. 3), and the result of PCR on negative control (C of FIG. 3) for the target gene amplification using the superfamily-specific degenerate primer used in the present invention.

FIG. 4 illustrates the results of the phylum and genus analysis for identifying the microbial community of volcanic metagenomic sample as an example of a metagenome sample analyzed by the method of the present invention, FIG. 5 illustrates the results of electrophoresis analysis for identifying target genes after performing PCR using each of the superfamily-specific degenerate primers and metagenome samples by the method of the present invention.

FIG. 6 illustrates the results of the microorganism phylum analysis of each metagenome sample of a pyruvate kinase gene as an example of a gene analyzed by the method of the present invention.

BEST MODE

Figure 1:
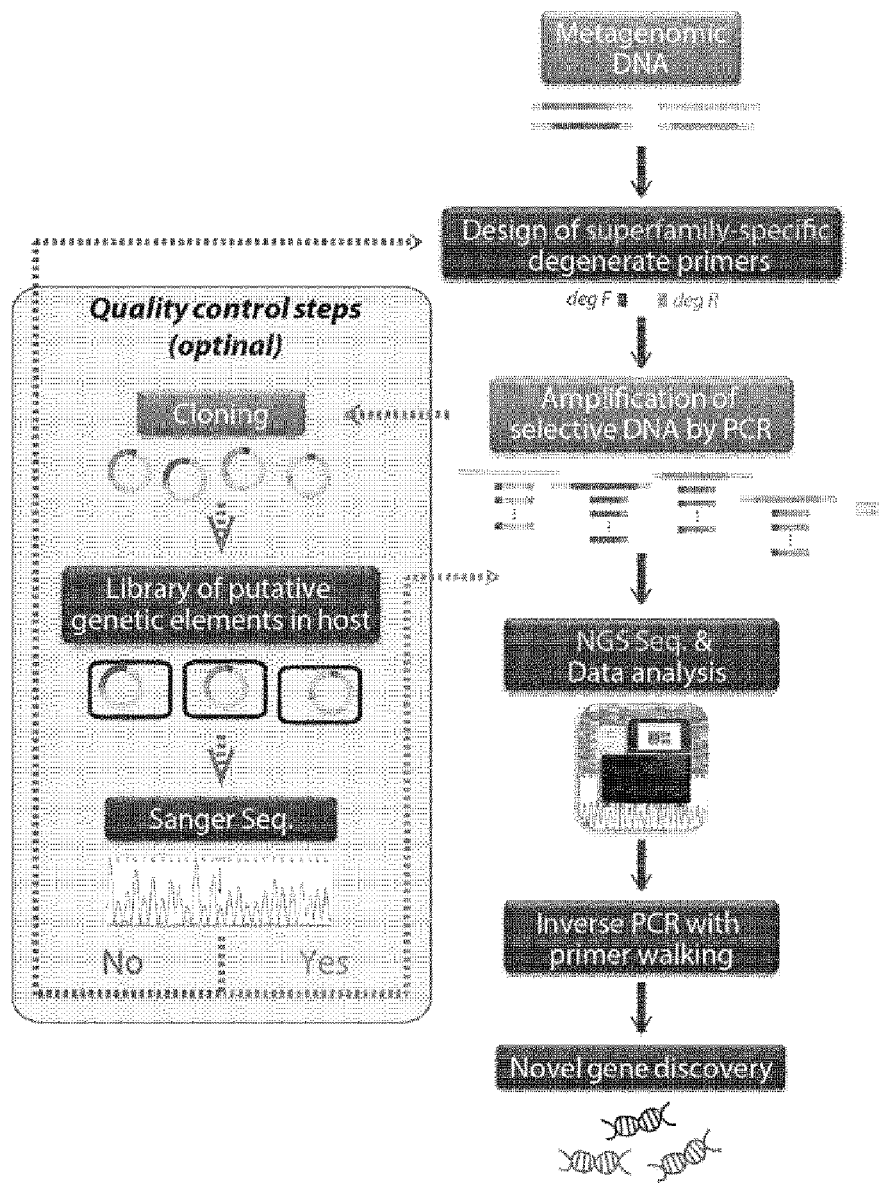
FIG. 1 illustrates an overall schematic diagram for describing a method of ultrahigh-speed large-capacity screening enzyme through analysis of massive amount of metagenomic information of the present invention.

An aspect of the present invention provides a method of analyzing metagenomic information, the method including the steps of:

(1) amplifying a gene in a metagenome sample, which is a template, with a superfamily-specific degenerate primer set to a target gene; and (2) analyzing sequence of the amplificatied product of the gene.

The superfamily-specific degenerate primer set to the target gene may be such that i) the primer set is specific for a gene encoding a target protein exhibiting amino acid identity of 35% or more;

ii) sequence of the binding site between the primer and the target gene has identity of 80% or more;

iii) a degeneracy ratio is 1,500 or less;

iv) a temperature of annealing is 70° C. or less;

v) a length of the primer is 30 bases or less;

vi) identity of an inside of the primer binding site is 40% or less; and vii) a size of the amplified fragment is 1,000 bp or less.

Preferably, the primer may be such that i) the primer set is specific for a gene encoding a target protein exhibiting amino acid identity of from 35% to 100%;

ii) sequence of the binding site between the primer and the target gene has identity of from 80% to 100%;

iii) a degeneracy ratio is from 0 to 1,500;

iv) a temperature of annealing is from 30° C. to 70° C.;

v) a length of the primer is from 4 bases to 30 bases;

vi) identity of an inside of the primer binding site is from 0% to 40%; and vii) a size of the amplified fragment is from 100 bp to 1,000 bp.

More preferably, the primer set may be such that the degeneracy ratio is from 0 to 800;

the length of the primer is from 4 bases to 25 bases; and the size of the amplified fragment is from 100 bp to 500 bp.

The metagenome sample may be a metagenomic library, a vector which the metagenomic library is introduced, or a cell transformed with the vector.

The metagenome sample may be a soil, a wetland, a volcano, a tidal mudflat, a salt pan, fresh water, seawater, a body fluid, urine, an agricultural product, an aquatic product, or feces.

The metagenomic library may be obtained by collecting microorganism populations present in a natural or specific area, extracting genome directly, and introducing it into a vector. The vector may be a plasmid, a fosmid, a cosmid, a bacterial artificial chromosome (BAC), a yeast artificial chromosome (YAC), or the like depending on the purpose of the user.

Further, the target gene may encode a polypeptide, an oligopeptide, an enzyme, an antibiotic resistance gene, an antimicrobial peptide, an antifungal peptide, an oligopeptide, or a marker.

The polypeptide, peptide, or oligopeptide may be a polymer of an amino acid through a peptide bond, and the peptide may be an enzyme, an antimicrobial peptide, or a marker.

The antimicrobial peptide exhibits an antibiotic effect against bacteria, fungi, protozoa, viruses, and the like and may be bacteriocin, defensin, indolicidin, cathelicidin, lactoferricin, lysozyme, and the like, and the kind thereof is not limited.

The enzyme may be selected from the group consisting of catalase hydroperoxidase II (KatE), catalase hydroperoxidase I (CatA), 4-aminobutyrate transaminase (GabT), UDP-N-acetylglucosamine-2-epimerase (WegB), L-arabinose isomerase (AraA), phytase (Phy), subtilisin (AprE), cellulase-1 (YtoP), cellulase-2 (EglS), triosephosphate isomerase (TpiA), pyruvate kinase (PyrK), and the like, and the kind thereof is not limited.

The marker is a tracer for predicting and diagnosing disease onset, prognosis, genotypes, sensitivity to medicines, and the like, and there is no limitation on the kind of diseases.

Further, the target gene may be an antibiotic resistance gene.

The antibiotic resistance may be a medicine resistance that even when a microorganism is exposed to an antibiotic, it can survive, which can be induced by various genetic modifications. The antibiotic may be ampicillin, aminoglycoside, beta-lactam, erythromycin, meticillin, vancomycin, quinolone-based antibiotic, and the like, and the kind thereof is not limited.

Further, the step (2) of analyzing the sequence uses one or more processes selected from the group consisting of single-molecule real-time sequencing, ion semiconductor sequencing, pyrosequencing, sequencing by synthesis (SBS), sequencing by ligation (SBL), and chain termination.

Further, another aspect of the present invention provides a superfamily-specific degenerate primer set to a target gene for analyzing metagenomic information in which i) the primer set is specific for a gene encoding a target protein exhibiting amino acid identity of 35% or more;

ii) sequence of the binding site between the primer and the target gene has identity of 80% or more;

iii) a degeneracy ratio is 1,500 or less;

iv) a temperature of annealing is 70° C. or less;

v) a length of the primer is 30 bases or less;

vi) identity of an inside of the primer binding site is 40% or less; and vii) a size of the amplified fragment is 1,000 bp or less.

The primer set may preferably be such that i) the primer set is specific for a gene encoding a target protein exhibiting amino acid identity of from 35% to 100%;

ii) sequence of the binding site between the primer and the target gene has identity of from 80% to 100%;

iii) a degeneracy ratio is from 0 to 1,500;

iv) a temperature of annealing is from 30° C. to 70° C.;

v) a length of the primer is from 4 bases to 30 bases;

vi) identity of an inside of the primer binding site is from 0% to 40%; and vii) a size of the amplified fragment is from 100 bp to 1,000 bp.

The primer set may more preferably be such that the degeneracy ratio is from 0 to 800;

the length of the primer is from 4 bases to 25 bases; and the size of the amplified fragment is from 100 bp to 500 bp.

The term "primer" as used herein refers to a synthetic or natural oligonucleotide. The primer serves as an initial point for the synthesis under conditions in which the synthesis of primer extension products complementary to the nucleic acid chain (template) is induced, that is, the presence of a polymerizing agent such as nucleotides and DNA polymerase, and a suitable temperature and pH. For maximum efficiency of amplification, the primer is preferably single-stranded. Preferably, the primer is an oligodeoxyribonucleotide. The primer of the present invention may include naturally occurring dNMP (that is, dAMP, dGMP, dCMP, and dTMP), modified nucleotide, or non-natural nucleotide.

Preferably, the superfamily-specific degenerate primer set to the target gene of the present invention includes a forward degenerate primer consisting of the nucleotide sequences shown in SEQ ID NO: 1 and a reverse degenerate primer set consisting of the nucleotide sequences shown in SEQ ID NO: 2; a forward degenerate primer consisting of the nucleotide sequences shown in SEQ ID NO: 3 and a reverse degenerate primer set consisting of the nucleotide sequences shown in SEQ ID NO: 4; a forward degenerate primer consisting of the nucleotide sequences shown in SEQ ID NO: 5 and a reverse degenerate primer set consisting of the nucleotide sequences shown in SEQ ID NO: 6; a forward degenerate primer consisting of the nucleotide sequences shown in SEQ ID NO: 7 and a reverse degenerate primer set consisting of the nucleotide sequences shown in SEQ ID NO: 8; a forward degenerate primer consisting of the nucleotide sequences shown in SEQ ID NO: 9 and a reverse degenerate primer set consisting of the nucleotide sequences shown in SEQ ID NO: 10; a forward degenerate primer consisting of the nucleotide sequences shown in SEQ ID NO: 11 and a reverse degenerate primer set consisting of the nucleotide sequences shown in SEQ ID NO: 12; a forward degenerate primer consisting of the nucleotide sequences shown in SEQ ID NO: 13 and a reverse degenerate primer set consisting of the nucleotide sequences shown in SEQ ID NO: 14; a forward degenerate primer consisting of the nucleotide sequences shown in SEQ ID NO: 15 and a reverse degenerate primer set consisting of the nucleotide sequences shown in SEQ ID NO: 16; a forward degenerate primer consisting of the nucleotide sequences shown in SEQ ID NO: 17 and a reverse degenerate primer set consisting of the nucleotide sequences shown in SEQ ID NO: 18; a forward degenerate primer consisting of the nucleotide sequences shown in SEQ ID NO: 19 and a reverse degenerate primer set consisting of the nucleotide sequences shown in SEQ ID NO: 20; or a forward degenerate primer consisting of the nucleotide sequences shown in SEQ ID NO: 21 and a reverse degenerate primer set consisting of the nucleotide sequences shown in SEQ ID NO: 22. It may be varied depending on the sequence of the target gene and thus is not limited to the sequence of the target gene.

Further, IUB ambiguity codes are used in representing the sequence of the primer. Thus, in the primer sequence, A represents adenine, G represents guanine, C represents cytosine, and T represents thymine. Further, R represents G or A, Y represents T or C, M represents A or C, K represents G or T, S represents G or C, W represents A or T, B represents G or C or T, D represents A or G or T, H represents A or C or T, V represents A or G or C, and N represents A or G or C or T. These apply equally to presenting all the sequences in this specification.

Further, still another aspect of the present invention provides a kit for metagenomic analysis, which includes the primer set as described above.

The kit of the present invention may include a reagent necessary for PCR reaction, for example a buffer, a DNA polymerase, a DNA polymerase associated factor, and a deoxyribonucleotide-5'-triphosphate. Optionally, the kit of the present invention may include various polynucleotide molecules, reverse transcriptase, various buffers and reagents, an antibody that inhibits the activity of DNA polymerase.

The optimal amount of reagent used in a certain reaction may be readily determined by one of ordinary skill in the art understanding content of the specification. Typically, the kit of the present invention includes the components as described above in the separated packages or divided compartments.

Further, still another aspect of the present invention provides a method of screening superfamily-specific degenerate primer set to a target gene for metagenomic information analysis, which includes the step of screening nucleotide sequence which satisfies conditions as described below:

i) the primer set is specific for a gene encoding a target protein exhibiting amino acid identity of 35% or more;

ii) sequence of the binding site between the primer and the target gene has identity of 80% or more;

iii) a degeneracy ratio is 1,500 or less;

iv) a temperature of annealing is 70° C. or less;

v) a length of the primer is 30 bases or less;

vi) identity of an inside of the primer binding site is 40% or less; and vii) a size of the amplified fragment is 1,000 bp or less.

Preferably, the method of screening superfamily-specific degenerate primer set to a target gene for metagenomic information analysis includes the step of screening nucleotide sequence which satisfies conditions as described below:

i) the primer set is specific for a gene encoding a target protein exhibiting amino acid identity of from 35% to 100%;

ii) sequence of the binding site between the primer and the target gene has identity of from 80% to 100%;

iii) a degeneracy ratio is from 0 to 1,500;

iv) a temperature of annealing is from 30° C. to 70° C.;

v) a length of the primer is from 4 bases to 30 bases;

vi) identity of an inside of the primer binding site is from 0% to 40%; and vii) a size of the amplified fragment is from 100 bp to 1,000 bp.

More preferably, the method of screening superfamily-specific degenerate primer set to a target gene for metagenomic information analysis includes the step of screening nucleotide sequence which satisfies conditions as described below:

the degeneracy ratio is from 0 to 800;

the length of the primer is from 4 bases to 25 bases; and the size of the amplified fragment is from 100 bp to 500 bp.

Hereinafter, it will be apparent to those skilled in the art that the examples are only for describing the present invention more specifically, and the scope of the present invention is not limited by these examples in accordance with the concept of the present invention.

Preparation Example: Preparation of Superfamily-Specific Degenerate Primer

In the present invention, catalase hydroperoxidase II (KatE), catalase hydroperoxidase I (Cat A), 4-aminobutyrate transaminase (GabT), UDP-N-acetylglucosamine-2-epimerase (WegB), L-arabinose isomerase (AraA), phytase (Phy), subtilisin (AprE), cellulase1 (YtoP), cellulase2

(EglS), triosephosphate isomerase (TpiA), and pyruvate kinase (PyrK) enzymes were selected as an example of target peptides, and their genetic informations were used. Under a condition that amino acid sequences have identity of 35% or more to the target protein, amino acid sequences of the respective enzyme genes were aligned. Subsequently, amino acid sequences having the identity of 80% or more between the resultant amino acid sequences were selected, and nucleotide sequences encoding the same were confirmed. Then, the alignment was performed again. The degenerate primer was prepared based on the nucleotide sequences determined to satisfy the conditions of the degeneracy ratio of the superfamily-specific degenerate primer based on the complementarity of the nucleotide sequence (1,500 or less, preferably 800 or less, the annealing temperature (70° C. or less), a primer length (30 bases or less, preferably 25 bases or less), low identity of 40% or less in the nucleotide sequence inside the primer binding site, and a size of the amplified fragment of 1,000 bp or less (or optionally 500 bp or less).

The present invention provides a primer for amplifying catalase hydroperoxidase II (KatE) gene as described above, composed of a forward degenerate primer consisting of the nucleotide sequence shown in SEQ ID NO: 1 and a reverse degenerate primer consisting of the nucleotide sequence shown in SEQ ID NO: 2 which were prepared through the process as described above. Here, the forward degenerate primer and reverse degenerate primer include degenerate primers used to amplify genes of known enzymes, as well as degenerate primers which are presumed to amplify genes of known enzymes in the same method.

Further, specific examples of degenerate primers prepared by the same method other than the primer sets of SEQ ID NOS: 1 and 2 are described below:

catalase hydroperoxidase II F:
(SEQ ID NO: 1)
5'-CRC TTY GAY CAY GAR MGB ATY CC-3';

catalase hydroperoxidase II R:
(SEQ ID NO: 2)
5'-ATG AAR AAS ACH GGV AWG TTR TTB CC-3';

catalase hydroperoxidase I F:
(SEQ ID NO: 3)
5'-TGG CCN RTH AAG MAR AAR TAY GG-3';

catalase hydroperoxidase I R:
(SEQ ID NO: 4)
5'-ACR GTY TCY TCR TCR TTC ATN SCC-3';

4-aminobutyrate transaminase F:
(SEQ ID NO: 5)
5'-SCV GAR GCV GTY GAR AAC GC-3';

4-aminobutyrate transaminase R:
(SEQ ID NO: 6)
5'-GCC HTC DCC BTG HAY CGG YTC-3';

UDP-N-acetylglucosamine-2-epimerase F:
(SEQ ID NO: 7)
5'-TCA YGT BGA RGC BGG VYT GMG-3';

UDP-N-acetylglucosamine-2-epimerase R:
(SEQ ID NO: 8)
5'-TG HAY VCC DCC VGA RTC VGT-3';

L-arabinose isomerase F:
(SEQ ID NO: 9)
5'-GAA CYT NAA CCA RDC NGC NCA CGG-3';

L-arabinose isomerase R:
(SEQ ID NO: 10)
5'-CCA GTC DCC TTC NSC NSC RAA NCC-3';

Phytase F:
(SEQ ID NO: 11)
5'-ACN CKK AAA ACV GGY GAR GC-3';

Phytase R:
(SEQ ID NO: 12)
5'-CAR SAG RAA WAT YTC VGY MAG C-3';

Subtilisin F:
(SEQ ID NO: 13)
5'-CAC GGH ACN CAT KKN GCN GG-3';

Subtilisin R:
(SEQ ID NO: 14)
5'-GGA GWB GCC ATD SWB GTD CCG-3';

Cellulase-1 F:
(SEQ ID NO: 15)
5'-ATV TAY GTH ATH RTY GAY TGG C-3';

Cellulase-1 R:
(SEQ ID NO: 16)
5'-RTG HGT DSC BGH ATA RAA ATG-3';

Cellulase-2 F:
(SEQ ID NO: 17)
5'-GSN CAY WTG GAY GAR RTS GG-3';

Cellulase-2 R:
(SEQ ID NO: 18)
5'-CCN AHY TCY TCC TGN ACN GT-3';

Triosephosphate isomerase F:
(SEQ ID NO: 19)
5'-GGN GCV TMY ACH GGY GAR-3';

Triosephosphate isomerase R:
(SEQ ID NO: 20)
5'-GC CCA NAY NGG YTC RTA VGC-3';

Pyruvate kinase F:
(SEQ ID NO: 21)
5'-CGN HTN AAC TTY TCS CAY GG-3';

Pyruvate kinase R:
(SEQ ID NO: 22)
5'-CAT BSA STC DAG CAT YTG HGT CGC-3'.

Accordingly, an object of the present invention is to provide a pair of a forward degenerate primer and a reverse degenerate primer complementary to the nucleotide sequence of the conserved region present in the enzyme.

The degenerate primer of the present invention is for selectively amplifying and detecting a portion (over 80%) having high identity through the amino acid sequence analysis of enzyme genes belonging to a specific enzyme superfamily and binds to a sequence having high complementarity of the gene of the specific enzyme gene.

The 11 pairs of degenerate primers exemplified above were used to confirm whether or not the above-mentioned 11 enzymes are present in certain strains and metagenomes.

Example 1: Design and Preparation of Superfamily-Specific Degenerate Primer

After genes of representative microorganisms of various domains known to produce conventional catalase hydroperoxide II (KatE) as a target were searched in database to select, at least 5 kinds of amino acid sequences of the selected gene have been used for alignment. Among the amino acid sequences, the peptide having identity of 35% or more to target protein was firstly screened.

Sequences having identity of 80% or more among multiple genes were secondarily selected as regions for design of the degenerate primer. After the selected amino acid sequences having high identity were converted into nucleotide sequences, the degenerate primer was prepared based on nucleotide sequences determined to have the conditions as important factors for preparing the degenerate primer, which were limited to have a degenerate ratio (1,500 or less, preferably 800 or less), an annealing temperature (70° C. or less), and a primer length (30 bases or less, preferably 25 bases or less) and to have the nucleotide sequence inside the primer binding site having the identity of 40% or less and the size of the amplified fragment having 1,000 bp or less (preferably 500 bp or less). Other degenerate primers for detecting other known enzymes were also designed and prepared in the method as described above.

Figure 2:
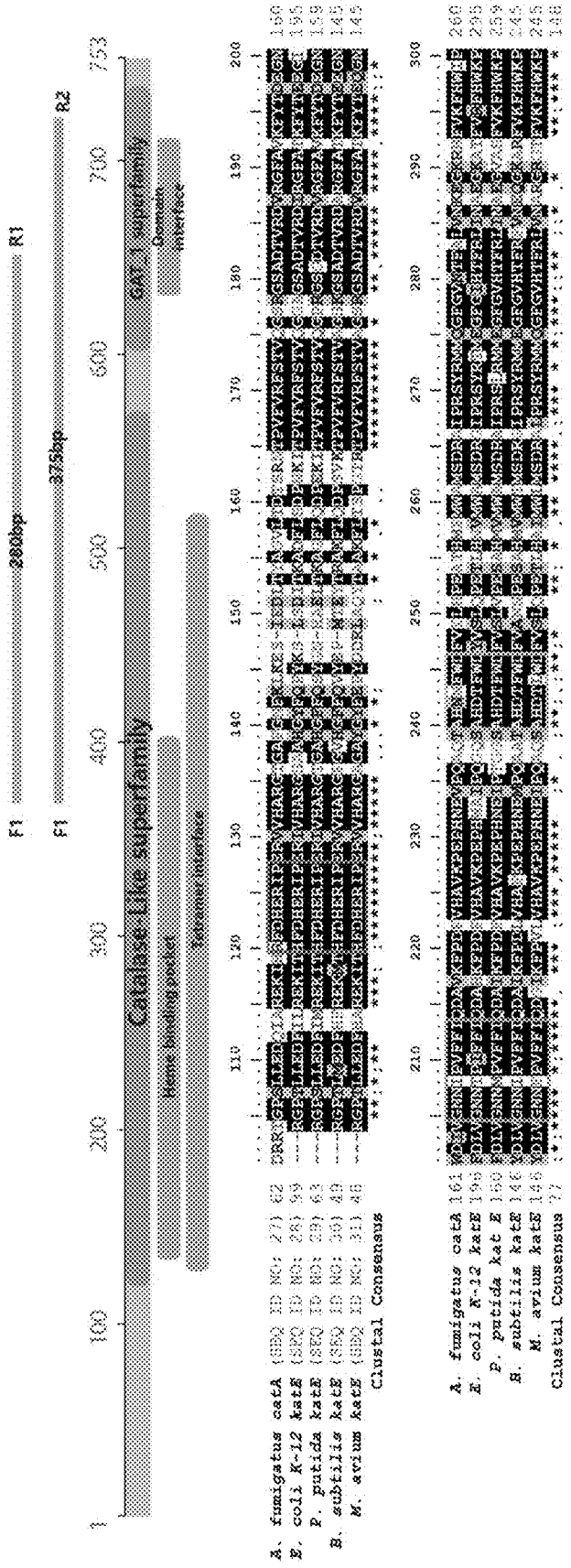
FIG. 2 illustrates a method of preparing a superfamily-specific degenerate primer used in the present invention.

An example of design of the degenerate primer is illustrated in FIG. 2.

Example 2: Polymerase Chain Reaction (PCR) and Confirmation of Amplified Gene Fragments In order to confirm whether the prepared degenerate primers for screening catalase hydroperoxidase II (KatE) (SEQ ID NO: 1: 5'-CRC TTY GAY CAY GAR MGB ATY CC-3' and SEQ ID NO: 2: 5'-ATG AAR AAS ACH GGV AWG TTR TTB CC-3') bind to a target gene, the polymerase chain reaction (PCR) was performed in which the genomic DNA of *Escherichia coli* MG1655, in which the amino acid sequence of the KatE gene was used for the production of the degenerate primer, was used as a template. The remaining degenerate primers were also subjected to the polymerase chain reaction (PCR) using the genomic DNA of *Escherichia coli* MG1655 as a template. Exceptionally, in order to confirm the binding of degenerate primers for subtilisin and cellulase detection to the target gene, the polymerase chain reaction (PCR) was performed using genomic DNA of *Bacillus subtilis* 168 rather than *Escherichia coli* MG1655, as a template.

The PCR reaction solution used herein was as follows: final 25 µl solution including 100 ng template (genomic DNA of obtained *Escherichia coli* MG1655 and *Bacillus subtilis* 168), 12.5 µl EmeraldAmp GT PCR Master Mix, 0.2 µM (final concentration) each forward and reverse degenerate primer, and sterilized distilled water. The PCR reaction was performed by 30 times of a cycle consisting of denaturation at 94° C. for 30 seconds, annealing at X° C. (for example, 54° C. of catalase hydroperoxidase II and catalase hydroperoxidase I; 58° C. of GABA transaminase, UDP-N-acetylglucosamine-2-epimerase, and L-arabinose isomerase; 52° C. of phytase and cellulase 2; 56° C. of subtilisin and pyruvate kinase, 51° C. of triosephosphate isomerase; and 47° C. of cellulase 1) for 30 seconds, and elongation 72° C. for 30 seconds. The PCR products were confirmed as in FIG. 3.

As illustrated in FIG. 3, the amplified PCR products were confirmed by performing electrophoresis on 2% agarose gel. The sizes of amplified gene fragments expected in *Escherichia coli* MG1655 and *Bacillus subtilis* 168 were confirmed (that is, about 280 bp catalase hydroperoxidase II; about 350 bp catalase hydroperoxidase I; about 300 bp GABA transaminase; about 540 bp UDP-N-acetylglucosamine-2-epimerase; about 570 bp L-arabinose isomerase; about 400 bp phytase; about 490 bp subtilisin; about 335 bp cellulase; about 300 bp triosephosphate isomerase; and about 760 bp pyruvate kinase).

Further, in order to confirm that the conditions described in the present invention are optimum, the PCR was performed by setting the annealing temperature at 70° C. or higher in the PCR reaction condition as a negative control group. As a result, as illustrated in FIG. 3C, when the annealing temperature was 70° C. or higher, it was confirmed that the target fragments were not amplified.

Example 3: Analysis of Nucleotide Sequences of Amplified Gene

The PCR product was purified using Qiaquick Gel extraction kit (QIAGEN, Germany) and ligated to a pGEM T-easy vector (Promega, USA) to construct vectors pGEM T-katE, catA, gabT, wegB, araA, phy, aprE, ytoP, eglS, tpiA, and pyrK including genes encoding catalase hydroperoxidase II, catalase hydroperoxidase I, GABA transaminase, UDP-N-acetylglucosamine-2-epimerase, L-arabinose isomerase, phytase, subtilisin, cellulase, triosephosphate isomerase, and pyruvate kinase of *Escherichia coli* MG1655.

Further, the recombinant vector was mixed with 100 µl of *Escherichia coli* DH5 (competent cells) prepared for transformation, and then the transformed *Escherichia coli* into which the vector was introduced was heat-shocked at 42° C. for 90 seconds, and plated on LB medium including 100 µg/ml ampicillin, thereby screening transformed *Escherichia coli*. In order to recover plasmid DNA, a plasmid extraction kit (Biofact, Korea) was used to recover the plasmid DNA, and the nucleotide sequence analysis was commissioned by Solgent (Korea). As a result of the nucleotide sequence analysis, it was confirmed that the PCR products are the same as genes of the enzymes included in *Escherichia coli* MG1655 and *Bacillus subtilis* 168.

Example 4: Polymerase Chain Reaction (PCR) of the Metagenome and Confirmation of Amplified Gene Fragments After confirming the binding ability of the prepared degenerate primers to the target gene, a polymerase chain reaction was carried out for screening the target gene using the metagenome as a template. The PCR reaction solutions used were as follows: final 25 µl solution including 100 ng template (metagenomic DNA of obtained Soil), 12.5 µl EmeraldAmp GT PCR Master Mix, 0.2 µM (final concentration) each forward and reverse degenerate primer, and sterilized distilled water. The PCR reaction was performed by 30 times of a cycle consisting of denaturation at 94° C. for 30 seconds, annealing at X° C. (for example, 54° C. of catalase hydroperoxidase II and catalase hydroperoxidase I; 58° C. of GABA transaminase, UDP-N-acetylglucosamine-2-epimerase, and L-arabinose isomerase; 52° C. of phytase and cellulase 2; 56° C. of subtilisin and pyruvate kinase, 51° C. of triosephosphate isomerase; and 47° C. of cellulase 1) for 30 seconds, and elongation 72° C. for 30 seconds. The PCR products were confirmed as in FIG. 5.

As illustrated in FIG. 5, the amplified PCR products were confirmed by performing electrophoresis on 2% agarose gel. Lane 1 is the amplified PCR product of encoded gene.

Example 5: Analysis of Nucleotide Sequence of Gene Amplified in Metagenome

The amplification patterns of various target genes were confirmed by polymerase chain reaction using 8 kinds of metagenomes as templates. Before using the next generation sequencing apparatus, in order to confirm the binding ability of the degenerate primers prepared in the PCR with the metagenome as a template to the target genes, PCR was performed using the Soil A metagenome as a template, thereby obtaining the amplified fragments (about 300 bp catalase hydroperoxidase II, about 350 bp catalase hydroperoxidase I, about 300 bp GABA transaminase), which were purified using a Qiaquick Gel extraction kit (QIAGEN, Germany), cloned into a pGEM T-easy vector, and subjected to sequencing by general sanger sequencing. As a result, it was confirmed that the target enzyme genes are detected, in addition, various strains including genes of the enzymes are detected through the Blast search result on the national center for biotechnology information (NCBI) website.

After confirming that information of various target genes can be collected from the metagenome through the experiment as described above, amplified fragments obtained by PCR using 8 kinds of metagenomes as templates were again used as templates for a sufficient amount to utilize the next-generation sequencing apparatus, and the superfamily-specific degenerate primer suitable for each enzyme was used, thereby re-performing the PCR under the condition for performing PCR as described in Example 4. After the amplified PCR products were collected, the amplified PCR products were collected for each of the metagenomes, and the nucleotide sequences as a total of 8 samples were analyzed using a next generation sequencing apparatus (Miseq). Since various kinds of PCR products were mixed in one metagenome, nucleotide sequences of the superfamily-specific degenerate primers were used as barcode sequences, thereby isolating and analyzing nucleotide sequences for the analysis of the nucleotide sequence.

Tables 1 and 2 as described below show the results of analyzing gene information of a plurality of metagenomic samples obtained using the metagenomic information analysis method according to the present invention.

TABLE 1

Numbers of phylum and genus according to microbial community analysis of analytical metagenome sample

|  | Phylum | Genus |
|---|---|---|
| Ind | 6 | 26 |
| Halo | 5 | 38 |
| HFD | 7 | 25 |
| HFD-M | 8 | 33 |
| Upo | 53 | 1064 |
| Soil A | 69 | 1633 |
| SB | 23 | 380 |
| New-R | 32 | 888 |

TABLE 2

Numbers of phylum and genus of each target enzyme according to analytical metagenome sample

|  |  | Ind | Halo | HFD | HFD-M | Upo | Soil A | SB | New-R |
|---|---|---|---|---|---|---|---|---|---|
| PyrK | Phylum | 18 | 12 | 22 | 22 | 31 |  | 31 |  |
|  | Genus | 222 | 252 | 363 | 501 | 961 |  | 841 |  |
| TpiA | Phylum | 22 | 18 | 18 | 20 | 35 | 37 |  | 18 |
|  | Genus | 352 | 139 | 193 | 238 | 965 | 1078 |  |  |
| KatE | Phylum | 16 | 16 |  |  | 30 | 23 |  |  |
|  | Genus | 209 | 286 |  |  | 792 | 577 |  | 478 |
| CatA | Phylum | 19 | 14 | 18 | 22 | 24 | 27 | 27 | 19 |
|  | Genus | 178 | 218 | 334 | 384 | 661 | 601 | 525 | 548 |
| GabT | Phylum | 18 | 12 | 17 |  |  | 32 | 99 | 14 |
|  | Genus | 113 | 130 | 265 |  |  | 882 | 326 | 258 |
| Wegß | Phylum | 17 |  | 21 | 19 |  |  |  |  |
|  | Genus | 145 |  | 287 | 276 |  |  |  |  |
| AraA | Phylum | 12 | 11 |  | 14 | 19 | 29 |  |  |
|  | Genus | 81 | 77 |  | 199 | 213 | 571 |  |  |
| Phy | Phylum |  |  |  | 18 |  |  |  |  |
|  | Genus |  |  |  | 275 |  |  |  |  |
| AprE | Phylum | 15 |  |  |  |  |  |  |  |
|  | Genus | 83 |  |  |  |  |  |  |  |
| YtoP | Phylum | 17 | 14 | 21 | 17 | 34 | 31 |  | 14 |
|  | Genus | 162 | 218 | 251 | 269 |  |  |  | 258 |
| EglS | Phylum | 17 | 11 | 15 | 17 |  |  |  |  |
|  | Genus | 134 | 194 | 172 | 211 | 825 | 738 |  |  |

Further, a method for analyzing the metagenome gene information according to the present invention is illustrated in FIG. 1. FIG. 1 illustrates a method of ultrahigh-speed large-capacity screening enzyme through analysis of massive amount of metagenomic information according to the present invention.

By the experiments as described above, the method for the metagenomic information analysis and the primer set used for the method according to the present invention can be applied for quickly determining the utility value of a massive amount of metagenome samples. In particular, the superfamily-specific degenerate primer of the present invention is used to quickly detect the presence or absence of the genetic information of the target peptides in the metagenome by a simple method, thereby collecting a large amount of useful peptide resource information from various metagenome samples at high speed. Further, the present invention may be used for screening new peptide genes by designing and producing superfamily-specific degenerate primers of new target peptides based on the method of the present invention. In addition, the method of the present invention can be applied not only to enzymes but also to studies related to polypeptides, oligopeptides, antibiotic resistance genes, antimicrobial peptides, antifungal peptides, oligopeptides, markers, or single-nucleotide polymorphism (SNP).

SEQUENCE LISTING

<160> NUMBER OF SEQ ID NOS: 31

<210> SEQ ID NO 1
<211> LENGTH: 23
<212> TYPE: DNA
<213> ORGANISM: Artificial Sequence
<220> FEATURE:
<223> OTHER INFORMATION: catalase HydroperoxidaseII F

<400> SEQUENCE: 1
crcttygayc aygarmgbat ycc                                             23

<210> SEQ ID NO 2
<211> LENGTH: 26
<212> TYPE: DNA
<213> ORGANISM: Artificial Sequence
<220> FEATURE:
<223> OTHER INFORMATION: catalase HydroperoxidaseII R

<400> SEQUENCE: 2
atgaaraasa chggvawgtt rttbcc                                          26

<210> SEQ ID NO 3
<211> LENGTH: 23
<212> TYPE: DNA
<213> ORGANISM: Artificial Sequence
<220> FEATURE:
<223> OTHER INFORMATION: catalase HydroperoxidaseI F
<220> FEATURE:
<221> NAME/KEY: misc_feature
<222> LOCATION: (6)..(6)
<223> OTHER INFORMATION: n is a, c, g, or t

<400> SEQUENCE: 3
tggccnrtha agmaraarta ygg                                             23

<210> SEQ ID NO 4
<211> LENGTH: 24
<212> TYPE: DNA
<213> ORGANISM: Artificial Sequence
<220> FEATURE:
<223> OTHER INFORMATION: catalase HydroperoxidaseI R
<220> FEATURE:
<221> NAME/KEY: misc_feature
<222> LOCATION: (21)..(21)
<223> OTHER INFORMATION: n is a, c, g, or t

<400> SEQUENCE: 4
acrgtytcyt crtcrttcat nscc                                            24

<210> SEQ ID NO 5
<211> LENGTH: 20
<212> TYPE: DNA
<213> ORGANISM: Artificial Sequence
<220> FEATURE:
<223> OTHER INFORMATION: 4-aminobutyrate transaminase F

<400> SEQUENCE: 5
scvgargcvg tygaraacgc                                                 20

<210> SEQ ID NO 6
<211> LENGTH: 21
<212> TYPE: DNA
<213> ORGANISM: Artificial Sequence
<220> FEATURE:
<223> OTHER INFORMATION: 4-aminobutyrate transaminase R

<400> SEQUENCE: 6

```
gcchtcdccb tghaycggyt c                                              21

<210> SEQ ID NO 7
<211> LENGTH: 21
<212> TYPE: DNA
<213> ORGANISM: Artificial Sequence
<220> FEATURE:
<223> OTHER INFORMATION: UDP-N-acetylglucosamine-2-epimerase F

<400> SEQUENCE: 7
tcaygtbgar gcbggvytgm g                                              21

<210> SEQ ID NO 8
<211> LENGTH: 20
<212> TYPE: DNA
<213> ORGANISM: Artificial Sequence
<220> FEATURE:
<223> OTHER INFORMATION: UDP-N-acetylglucosamine-2-epimerase R

<400> SEQUENCE: 8
tghayvccdc cvgartcvgt                                                20

<210> SEQ ID NO 9
<211> LENGTH: 24
<212> TYPE: DNA
<213> ORGANISM: Artificial Sequence
<220> FEATURE:
<223> OTHER INFORMATION: L-arabinose isomerase F
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 9
gaacytnaac cardcngcnc acgg                                           24

<210> SEQ ID NO 10
<211> LENGTH: 24
<212> TYPE: DNA
<213> ORGANISM: Artificial Sequence
<220> FEATURE:
<223> OTHER INFORMATION: L-arabinose isomerase R
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 10
ccagtcdcct tcnscnscra ancc                                           24

<210> SEQ ID NO 11
<211> LENGTH: 20
<212> TYPE: DNA
```

```
<213> ORGANISM: Artificial Sequence
<220> FEATURE:
<223> OTHER INFORMATION: Phytase F
<220> FEATURE:
<221> NAME/KEY: misc_feature
<222> LOCATION: (3)..(3)
<223> OTHER INFORMATION: n is a, c, g, or t

<400> SEQUENCE: 11
acnckkaaaa cvggygargc                                                    20

<210> SEQ ID NO 12
<211> LENGTH: 22
<212> TYPE: DNA
<213> ORGANISM: Artificial Sequence
<220> FEATURE:
<223> OTHER INFORMATION: Phytase R

<400> SEQUENCE: 12
carsagraaw atytcvgyma gc                                                 22

<210> SEQ ID NO 13
<211> LENGTH: 20
<212> TYPE: DNA
<213> ORGANISM: Artificial Sequence
<220> FEATURE:
<223> OTHER INFORMATION: Subtilisin F
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 13
cacgghacnc atkkngcngg                                                    20

<210> SEQ ID NO 14
<211> LENGTH: 21
<212> TYPE: DNA
<213> ORGANISM: Artificial Sequence
<220> FEATURE:
<223> OTHER INFORMATION: Subtilisin R

<400> SEQUENCE: 14
ggagwbgcca tdswbgtdcc g                                                  21

<210> SEQ ID NO 15
<211> LENGTH: 22
<212> TYPE: DNA
<213> ORGANISM: Artificial Sequence
<220> FEATURE:
<223> OTHER INFORMATION: Cellulase-1 F

<400> SEQUENCE: 15
atvtaygtha thrtygaytg gc                                                 22

<210> SEQ ID NO 16
<211> LENGTH: 21
<212> TYPE: DNA
<213> ORGANISM: Artificial Sequence
<220> FEATURE:
<223> OTHER INFORMATION: Cellulase-1 R
```

<400> SEQUENCE: 16
rtghgtdscb ghataraaat g                                                 21

<210> SEQ ID NO 17
<211> LENGTH: 20
<212> TYPE: DNA
<213> ORGANISM: Artificial Sequence
<220> FEATURE:
<223> OTHER INFORMATION: Cellulase-2 F
<220> FEATURE:
<221> NAME/KEY: misc_feature
<222> LOCATION: (3)..(3)
<223> OTHER INFORMATION: n is a, c, g, or t

<400> SEQUENCE: 17
gsncaywtgg aygarrtsgg                                                   20

<210> SEQ ID NO 18
<211> LENGTH: 20
<212> TYPE: DNA
<213> ORGANISM: Artificial Sequence
<220> FEATURE:
<223> OTHER INFORMATION: Cellulase-2 R
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 18
ccnahytcyt cctgnacngt                                                   20

<210> SEQ ID NO 19
<211> LENGTH: 18
<212> TYPE: DNA
<213> ORGANISM: Artificial Sequence
<220> FEATURE:
<223> OTHER INFORMATION: Triosephosphate isomerase F
<220> FEATURE:
<221> NAME/KEY: misc_feature
<222> LOCATION: (3)..(3)
<223> OTHER INFORMATION: n is a, c, g, or t

<400> SEQUENCE: 19
ggngcvtmya chggygar                                                     18

<210> SEQ ID NO 20
<211> LENGTH: 20
<212> TYPE: DNA
<213> ORGANISM: Artificial Sequence
<220> FEATURE:
<223> OTHER INFORMATION: Triosephosphate isomerase R
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 20
gcccanayng gytcrtavgc                                          20

<210> SEQ ID NO 21
<211> LENGTH: 20
<212> TYPE: DNA
<213> ORGANISM: Artificial Sequence
<220> FEATURE:
<223> OTHER INFORMATION: Pyruvate kinase F
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 21
cgnhtnaact tytcscaygg                                          20

<210> SEQ ID NO 22
<211> LENGTH: 24
<212> TYPE: DNA
<213> ORGANISM: Artificial Sequence
<220> FEATURE:
<223> OTHER INFORMATION: Pyruvate kinase R

<400> SEQUENCE: 22
catbsastcd agcatytghg tcgc                                     24

<210> SEQ ID NO 23
<211> LENGTH: 20
<212> TYPE: DNA
<213> ORGANISM: Artificial Sequence
<220> FEATURE:
<223> OTHER INFORMATION: Pyruvate kinase R-2
<220> FEATURE:
<221> NAME/KEY: misc_feature
<222> LOCATION: (9)..(9)
<223> OTHER INFORMATION: n is a, c, g, or t

<400> SEQUENCE: 23
tcccavarnk trtcrtgvgc                                          20

<210> SEQ ID NO 24
<211> LENGTH: 7
<212> TYPE: PRT
<213> ORGANISM: Artificial Sequence
<220> FEATURE:
<223> OTHER INFORMATION: conserved AA seq.
<220> FEATURE:
<221> NAME/KEY: MISC_FEATURE
<222> LOCATION: (1)..(1)
<223> OTHER INFORMATION: Xaa is any amino acid

<400> SEQUENCE: 24

Xaa Phe Asp His Glu Arg Ile
 1               5

<210> SEQ ID NO 25
<211> LENGTH: 9
<212> TYPE: PRT
<213> ORGANISM: Artificial Sequence
<220> FEATURE:
<223> OTHER INFORMATION: conserved AA seq.
<220> FEATURE:
<221> NAME/KEY: MISC_FEATURE
<222> LOCATION: (4)..(4)
<223> OTHER INFORMATION: Xaa is any amino acid

<400> SEQUENCE: 25

Gly Asn Asn Xaa Pro Val Phe Phe Ile
1               5

<210> SEQ ID NO 26
<211> LENGTH: 7
<212> TYPE: PRT
<213> ORGANISM: Artificial Sequence
<220> FEATURE:
<223> OTHER INFORMATION: conserved AA seq.
<220> FEATURE:
<221> NAME/KEY: MISC_FEATURE
<222> LOCATION: (3)..(5)
<223> OTHER INFORMATION: all Xaa is independently any amino acid

<400> SEQUENCE: 26

Ala His Xaa Xaa Xaa Trp Asp
1               5

<210> SEQ ID NO 27
<211> LENGTH: 199
<212> TYPE: PRT
<213> ORGANISM: Artificial Sequence
<220> FEATURE:
<223> OTHER INFORMATION: A. fumigatus catA

<400> SEQUENCE: 27

Asp Arg Arg Thr Gly Pro Ser Leu Leu Glu Asp Gln Ile Ala Arg Glu
1               5                   10                  15

Lys Ile His Arg Phe Asp His Glu Arg Ile Pro Glu Arg Val Val His
            20                  25                  30

Ala Arg Gly Thr Gly Ala Phe Gly Asn Phe Lys Leu Lys Glu Ser Ile
        35                  40                  45

Glu Asp Leu Thr Tyr Ala Gly Val Leu Thr Asp Thr Ser Arg Asn Thr
    50                  55                  60

Pro Val Phe Val Arg Phe Ser Thr Val Gln Gly Ser Arg Gly Ser Ala
65                  70                  75                  80

Asp Thr Val Arg Asp Val Arg Gly Phe Ala Val Lys Phe Tyr Thr Asp
                85                  90                  95

Glu Gly Asn Trp Asp Ile Val Gly Asn Asn Ile Pro Val Phe Phe Ile
            100                 105                 110

Gln Asp Ala Val Lys Phe Pro Asp Phe Val His Ala Val Lys Pro Glu
        115                 120                 125

Pro His Asn Glu Val Pro Gln Ala Gln Thr Ala His Asn Asn Phe Trp
    130                 135                 140

Asp Phe Val Tyr Leu His Pro Glu Ala Thr His Met Phe Met Trp Ala
145                 150                 155                 160

Met Ser Asp Arg Ala Ile Pro Arg Ser Tyr Arg Met Met Gln Gly Phe
                165                 170                 175

Gly Val Asn Thr Phe Ala Leu Val Asn Lys Glu Gly Lys Arg His Phe
            180                 185                 190

Val Lys Phe His Trp Ile Pro
        195

<210> SEQ ID NO 28
<211> LENGTH: 196
<212> TYPE: PRT
<213> ORGANISM: Artificial Sequence
<220> FEATURE:
<223> OTHER INFORMATION: E. coli K-12 katE

<400> SEQUENCE: 28

```
Arg Gly Pro Thr Leu Leu Glu Asp Phe Ile Leu Arg Glu Lys Ile Thr
1               5                   10                  15

His Phe Asp His Glu Arg Ile Pro Glu Arg Ile Val His Ala Arg Gly
            20                  25                  30

Ser Ala Ala His Gly Tyr Phe Gln Pro Tyr Lys Ser Leu Ser Asp Ile
        35                  40                  45

Thr Lys Ala Asp Phe Leu Ser Asp Pro Asn Lys Ile Thr Pro Val Phe
    50                  55                  60

Val Arg Phe Ser Thr Val Gln Gly Gly Ala Gly Ser Ala Asp Thr Val
65                  70                  75                  80

Arg Asp Ile Arg Gly Phe Ala Thr Lys Phe Tyr Thr Glu Glu Gly Ile
                85                  90                  95

Phe Asp Leu Val Gly Asn Asn Thr Pro Ile Phe Ile Gln Asp Ala
            100                 105                 110

His Lys Phe Pro Asp Phe Val His Ala Val Lys Pro Glu Pro His Trp
        115                 120                 125

Ala Ile Pro Gln Gly Gln Ser Ala His Asp Thr Phe Trp Asp Tyr Val
    130                 135                 140

Ser Leu Gln Pro Glu Thr Leu His Asn Val Met Trp Ala Met Ser Asp
145                 150                 155                 160

Arg Gly Ile Pro Arg Ser Tyr Arg Thr Met Glu Gly Phe Gly Ile His
                165                 170                 175

Thr Phe Arg Leu Ile Asn Ala Glu Gly Lys Ala Thr Phe Val Arg Phe
            180                 185                 190

His Trp Lys Pro
        195
```

<210> SEQ ID NO 29
<211> LENGTH: 196
<212> TYPE: PRT
<213> ORGANISM: Artificial Sequence
<220> FEATURE:
<223> OTHER INFORMATION: P. putida katE

<400> SEQUENCE: 29

```
Arg Gly Pro Ser Leu Leu Glu Asp Phe Ile Met Arg Glu Lys Ile Thr
1               5                   10                  15

His Phe Asp His Glu Arg Ile Pro Glu Arg Ile Val His Ala Arg Gly
            20                  25                  30

Thr Gly Ala His Gly Phe Phe Gln Ser Tyr Gly Asn His Ala Glu Leu
        35                  40                  45

Thr Lys Ala Gly Phe Leu Gln Asp Pro Glu Lys Ile Thr Pro Val Phe
    50                  55                  60

Val Arg Phe Ser Thr Val Gln Gly Pro Arg Gly Ser Gly Asp Thr Val
65                  70                  75                  80

Arg Asp Val Arg Gly Phe Ala Val Lys Phe Tyr Thr Asp Glu Gly Asn
                85                  90                  95

Phe Asp Leu Val Gly Asn Asn Met Pro Val Phe Ile Gln Asp Ala
            100                 105                 110

Ile Lys Phe Pro Asp Phe Val His Ala Val Lys Pro Glu Pro His Asn
        115                 120                 125

Glu Ile Pro Thr Gly Gly Ser Ala His Asp Thr Phe Trp Asp Phe Val
    130                 135                 140

Ser Leu Val Pro Glu Ser Ala His Met Val Met Trp Ala Met Ser Asp
```

```
                145                 150                 155                 160
Arg Ala Ile Pro Arg Ser Leu Arg Met Met Glu Gly Phe Gly Val His
                165                 170                 175

Thr Phe Arg Leu Ile Asn Ala Glu Gly Val Ala Ser Phe Val Lys Phe
                180                 185                 190

His Trp Lys Pro
        195

<210> SEQ ID NO 30
<211> LENGTH: 196
<212> TYPE: PRT
<213> ORGANISM: Artificial Sequence
<220> FEATURE:
<223> OTHER INFORMATION: B. subtilis katE

<400> SEQUENCE: 30

Arg Gly Pro Thr Leu Met Glu Asp Phe His Phe Arg Glu Lys Met Thr
1               5                   10                  15

His Phe Asp His Glu Arg Ile Pro Glu Arg Val Val His Ala Arg Gly
                20                  25                  30

Phe Gly Val His Gly Phe Phe Gln Val Tyr Glu Pro Met Thr Glu Tyr
            35                  40                  45

Thr Arg Ala Lys Phe Leu Gln Asp Pro Ser Val Lys Thr Pro Val Phe
    50                  55                  60

Val Arg Phe Ser Thr Val Ala Gly Ser Lys Gly Ser Ala Asp Thr Val
65                  70                  75                  80

Arg Asp Ala Arg Gly Phe Ala Thr Lys Phe Tyr Thr Glu Glu Gly Asn
                85                  90                  95

Tyr Asp Leu Val Gly Asn Asn Ile Pro Val Phe Phe Ile Gln Asp Ala
                100                 105                 110

Ile Lys Phe Pro Asp Leu Val His Ala Phe Lys Pro Glu Pro His Asn
            115                 120                 125

Glu Met Pro Gln Ala Ala Thr Ala His Asp Thr Phe Trp Asp Phe Val
        130                 135                 140

Ala Asn Asn Pro Glu Ser Ala His Met Val Met Trp Thr Met Ser Asp
145                 150                 155                 160

Arg Gly Ile Pro Arg Ser Tyr Arg Met Met Glu Gly Phe Gly Val His
                165                 170                 175

Thr Phe Arg Phe Val Asn Glu Gln Gly Lys Ala Arg Phe Val Lys Phe
                180                 185                 190

His Trp Lys Pro
        195

<210> SEQ ID NO 31
<211> LENGTH: 197
<212> TYPE: PRT
<213> ORGANISM: Artificial Sequence
<220> FEATURE:
<223> OTHER INFORMATION: M. avium katE

<400> SEQUENCE: 31

Arg Gly Pro Thr Leu Leu Glu Asp Phe His Ala Arg Glu Lys Ile Thr
1               5                   10                  15

His Phe Asp His Glu Arg Ile Pro Glu Arg Val Val His Ala Arg Gly
                20                  25                  30

Ala Gly Ala Tyr Gly Tyr Phe Glu Pro Tyr Asp Asp Arg Leu Ala Gln
            35                  40                  45
```

-continued

| | | | | | | | | | | | | | | | |
|---|---|---|---|---|---|---|---|---|---|---|---|---|---|---|---|
| Tyr | Thr<br>50 | Ala | Ala | Lys | Phe<br>55 | Leu | Thr | Ser | Pro | Gly<br>60 | Thr | Arg | Thr | Pro | Val |
| Phe<br>65 | Val | Arg | Phe | Ser | Thr<br>70 | Val | Ala | Gly | Ser | Arg<br>75 | Gly | Ser | Ala | Asp | Thr<br>80 |
| Val | Arg | Asp | Val | Arg<br>85 | Gly | Phe | Ala | Thr | Lys<br>90 | Phe | Tyr | Thr | Glu | Gln<br>95 | Gly |
| Asn | Tyr | Asp | Leu<br>100 | Val | Gly | Asn | Asn | Phe<br>105 | Pro | Val | Phe | Phe | Ile<br>110 | Gln | Asp |
| Gly | Ile | Lys<br>115 | Phe | Pro | Val | Leu<br>120 | Val | His | Ala | Val | Lys<br>125 | Pro | Glu | Pro | His |
| Asn | Glu<br>130 | Ile | Pro | Gln | Ala<br>135 | Gln | Ser | Ala | His | Asp<br>140 | Thr | Leu | Trp | Asp | Phe |
| Val<br>145 | Ser | Leu | Gln | Pro | Glu<br>150 | Thr | Leu | His | Ala | Ile<br>155 | Met | Trp | Leu | Met | Ser<br>160 |
| Asp | Arg | Ala | Leu | Pro<br>165 | Arg | Ser | Tyr | Arg | Met<br>170 | Met | Gln | Gly | Phe | Gly<br>175 | Val |
| His | Thr | Phe | Arg<br>180 | Leu | Val | Asn | Ala | Arg<br>185 | Gly | Arg | Gly | Thr | Phe<br>190 | Val | Lys |
| Phe | His | Trp<br>195 | Lys | Pro | | | | | | | | | | | |

The invention claimed is:

1. A method of analyzing a metagenomic sample, the method comprising:
   (1) preparing a superfamily-specific degenerate primer set by:
      (i) selecting a plurality of genes each encoding a protein which has 35% or more amino acid sequence identity to a target protein encoded by a target gene, wherein sequence information of the plurality of genes, the target protein and the target gene is known prior to performing step (i);
      (ii) aligning respective amino acid sequences of the plurality of genes selected in step (i), and selecting a first sequence region and a second sequence region where the amino acid sequence identity between the respective amino acid sequences is 80% or more, wherein the sequence identity of the respective amino acid sequences at a region between the first sequence region and the second sequence region while excluding the first sequence region and the second sequence region is 40% or less; and
      (iii) producing the superfamily-specific degenerate primer set, which consists of a forward degenerate primer and a reverse degenerate primer, satisfying the following conditions:
      the forward degenerate primer binds to 3' end of an anti-sense strand of DNA encoding the first sequence region, and the reverse degenerate primer binds to 3' end of a sense strand of DNA encoding the second sequence region;
      the degeneracy of each of the forward degenerate primer and the reverse degenerate primer in the superfamily-specific degenerate primer set is less than 800;
      the annealing temperature of the superfamily-specific degenerate primer set is from 45° C. to 68° C.;
      the length of each of the forward degenerate primer and the reverse degenerate primer in the superfamily-specific degenerate primer set is from 18-30 nucleotides, and
   (2) providing the metagenomic sample;
   (3) conducting an amplification reaction using the superfamily-specific degenerate primer set and DNA from the metagenomic sample to produce an amplified DNA product; and
   (4) sequencing the amplified DNA product.

2. The method of claim 1, wherein the metagenomic sample is a metagenomic library, a vector into which the metagenomic library is introduced, or a cell transformed with the vector.

3. The method of claim 1, wherein the metagenomic sample is a soil sample, a wetland sample, a volcano sample, a tidal mudflat sample, a salt pan sample, a fresh water sample, a seawater sample, a body fluid sample, a urine sample, an agricultural product, an aquatic product, or a feces sample.

4. The method of claim 1, wherein step (34) is conducted by one or more processes selected from the group consisting of single-molecule real-time sequencing, ion semiconductor sequencing, pyrosequencing, sequencing-by-synthesis (SBS), sequencing-by-ligation (SBL), and chain termination.

* * * * *